US006387831B2

(12) United States Patent
Rhim et al.

(10) Patent No.: US 6,387,831 B2
(45) Date of Patent: *May 14, 2002

(54) COMPRESSED ABSORBENT COMPOSITES

(75) Inventors: Hannong Rhim, Roswell; Roland Columbus Smith, Jr., Gainesville, both of GA (US); Rob David Everett, Appleton, WI (US); Clifford Jackson Ellis, Woodstock; Christopher Cosgrove Creagan, Marietta, both of GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,222

(22) Filed: Nov. 16, 1998

Related U.S. Application Data

(60) Provisional application No. 60/068,766, filed on Dec. 23, 1997.
(51) Int. Cl.[7] .......................... D04H 1/00; D04H 13/00; D04H 3/00; D04H 5/00
(52) U.S. Cl. ....................... 442/414; 442/153; 442/329; 442/416
(58) Field of Search ............................ 442/414, 416, 442/153, 329

(56) References Cited

U.S. PATENT DOCUMENTS

| | | | | |
|---|---|---|---|---|
| 5,466,513 A | * | 11/1995 | Wanek et al. | 428/218 |
| 5,490,846 A | * | 2/1996 | Ellis et al. | 604/366 |
| 5,525,407 A | * | 6/1996 | Yang | 428/218 |
| 5,527,300 A | * | 6/1996 | Sauer | 604/378 |
| 5,665,082 A | | 9/1997 | Boulanger | 604/365 |
| 5,843,063 A | * | 12/1998 | Anderson et al. | 604/378 |
| 5,865,825 A | * | 2/1999 | Schlinz | 604/385.2 |
| 5,947,947 A | * | 9/1999 | Tanzer et al. | 604/385.1 |

FOREIGN PATENT DOCUMENTS

| | | | |
|---|---|---|---|
| EP | 0 162 451 | 11/1985 | A61F/13/16 |
| EP | 0 806 194 | 11/1997 | A61F/13/15 |

* cited by examiner

*Primary Examiner*—Terrel Morris
*Assistant Examiner*—Norca L. Torres
(74) *Attorney, Agent, or Firm*—James B. Robinson

(57) ABSTRACT

There is provided a fibrous web which includes a binder and which is compressed to a density of up to about 0.3 g/cc. The web may preferably be formed by the bonded carded web process or air lay process. The binder may depend on hydrogen bonding using moisture or may be a non-aqueous solution, a powder, a fibrous binder or a conjugate fiber binder including a moisture triggerable component. Conjugate fibers may be crimped. When wetted the web of this invention should expand rapidly to greater than 80% of its uncompressed thickness and greater than 90% of its thickness when saturated if starting from the uncompressed state.

15 Claims, No Drawings

COMPRESSED ABSORBENT COMPOSITES

This application claims priority from U.S. Provisional Application no. 60/068,766 filed Dec. 23, 1997.

FIELD OF THE INVENTION present invention relates to absorbent articles, particularly absorbent structures which are useful in personal care products such as disposable sanitary napkins, diapers, or incontinence guards. More particularly, the invention relates to absorbent articles which have a portion designed for rapid uptake, temporary liquid control, and subsequent release of repeated liquid surges to the remainder of the article.

BACKGROUND OF THE INVENTION

The desired performance objectives of personal care absorbent products include low or no leakage from the product, a dry feel to the wearer, and thinness as a means to provide comfort to the wearer. Current absorbent products, however, often fail to meet these objectives for a variety of reasons.

Leakage can occur, for example, due to insufficient uptake rate by layers intended to provide retention or distribution capability in the intake or target zone. Attempts to alleviate leakage occurring by this mechanism include absorbent articles that incorporate surge material structures located above (i.e., toward the wearer) the retention or distribution materials. U.S. Pat. No. 5,364,382 to Latimer discloses nonwoven materials such as meltblowns, bonded carded webs, and pulp conforms that receive and subsequently release liquid to the retention means. The material structures of Latimer utilize large denier resilient fibers blended with small denier wettable fibers to achieve rapid liquid uptake and rapid liquid release to the underlying retention storage material. Additionally, U.S. Pat. No. 5,490,846 to Ellis discloses layered structures to improve intake rates of surge materials.

Despite the development of surge materials that attempt to achieve rapid uptake and rapid release to the retention material, the objective of thinness remains to be satisfactorily reached. The cited surges are quite thick and when placed into the intake zone of the absorbent article can cause poor fit in the crotch region of the absorbent product upon initial wearing and can lead to several performance problems. Firstly, the product can leak due to gapping that is created by the bulky surge material. Secondly, the product is not comfortable to the wearer when a bulky material is utilized to provide the necessary void volume for uptake. There remains a need, therefore, for a surge material which will rapidly uptake an insult to the target area and release it for subsequent storage and which also remains relatively thin prior to insult.

It is an object of this invention to provide a surge material for personal care products which rapidly uptakes an insult and transfers it to an adjacent material for distribution or storage, and which remains relatively thin prior to initial insult. It is another object of this invention to provide a personal care product which, prior to insult, is thin and comfortable for a wearer.

SUMMARY OF THE INVENTION

The objectives of the invention are achieved by materials and products which have been designed to be very thin prior to insult and expand rapidly when insulted. In its broadest definition the invention is a fibrous web which includes a binder and which is compressed to a density of up to about 0.3 g/cc. The web may preferably be formed by the bonded carded web process, conform process or air lay process. The binder may depend on hydrogen bonding using moisture or may be a non-aqueous solution, a powder, a fibrous binder or a conjugate fiber binder including a moisture triggerable component. Conjugate fibers may be crimped. When wetted the web of this invention should expand rapidly to greater than 80% of its uncompressed thickness and greater than 90% of its thickness when saturated if starting from the uncompressed state.

DEFINITIONS

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous, non-particulate substance and/or material that flows and can assume the interior shape of a container into which it is poured or placed.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about $1.42 (15^2 \times 0.89 \times 0.00707 = 1.415)$. Outside the United States the unit of measurement is more commonly the "tex", which is defined as the grams per kilometer of fiber. Tex may be calculated as denier/9.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat.

No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "conform" means a process in which at least one meltblown diehead is arranged near a chute through which other materials are added to the web while it is forming. Such other materials may be wood pulp, superabsorbent particles, cellulose or staple fibers, for example. Conform processes are shown in commonly assigned U.S. Pat. No. 4,818,464 to Lau and U.S. Pat. No. 4,100,324 to Anderson et al. Webs produced by the conform process are generally referred to as conform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught, for example, in U.S. Pat. No. 5,382,400 to Pike et al. and may be used to produce crimp in the fibers by using the differential rates of expansion and contraction of the two (or more) polymers. Such fibers may also be splittable. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al. which describes fibers with unconventional shapes.

The methods for making conjugate fibers are well known and need not be described herein in detail. To form a conjugate fiber, generally, two polymers are extruded separately and fed to a polymer distribution system where the polymers are introduced into a segmented spinneret plate. The polymers follow separate paths to the fiber spinneret and are combined in a spinneret hole which comprises either two or more concentric circular holes thus providing a sheath/core type fiber or a circular spinneret hole divided along a diameter into two parts to provide a side-by-side type fiber. The combined polymer filament is then cooled, solidified and drawn, generally by a mechanical rolls system, to an intermediate filament diameter and collected. Subsequently, the filament is "cold drawn", at a temperature below its softening temperature, to the desired finished fiber diameter and is crimped/textured and cut into a desirable fiber length. Conjugate fibers can be cut into relatively short lengths, such as staple fibers which generally have lengths in the range of 25 to 51 millimeters (mm) and short-cut fibers which are even shorter and generally have lengths less than 18 millimeters. See, for example, U.S. Pat. No. 4,789,592 to Taniguchi et al. and U.S. Pat. No. 5,336,552 to Strack et al, both of which are incorporated herein by reference in their entirety "Bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, through-air bonding means a process of bonding a fiber web in which air which is sufficiently hot to melt the polymers of which the fibers of the web are made is forced through the web. The air velocity is between 100 and 500 feet per minute and the dwell time may be as long as 6 seconds. The melting and resolidification of the polymer provides the bonding.

"Personal care product" means diapers, training pants, absorbent underpants, feminine hygiene products and adult incontinence products.

DETAILED DESCRIPTION OF THE INVENTION

The material structures of this invention have been designed to be very thin materials that expand rapidly when insulted. When the user applies an absorbent article incorporating a material of this invention, it will be very thin and comfortable and facilitate good fit.

As the material structure expands during use, it should create the necessary void volume to accommodate incoming fluid which in turn will reduce the chances for leakage. The inventors believe that the area of the material which is just being wetted by the moving liquid front will have a high driving or capillary force causing movement of liquid into the material. The portion of the material which is already wetted and expanded will provide retention capacity and allow a greater flow rate of liquid through the wetted portion of the material.

There are several embodiments of this invention described below. All have been designed to begin with a very thin structure which then expands upon contact with the insult fluid. Also, it should be noted that the preferred use for this material is as a surge, it could function as a distribution material as well.

Material may be compressed from the as-produced low density state to a higher density thin state in the presence of up to about 10 weight percent moisture. It is believed that this would allow hydrogen bonds to form. Additional moisture, like that provided by an insult in a personal care product, should cause the hydrogen bonds to release and the material to expand an intake the liquid insult. The material may include cellulosic fibers like rayon or cotton in an amount from about 20 to 60 weight percent and non-cellulosic fibers like polyolefins, polyester, and polyamide fibers for the balance. Pulp fibers may be used, though are not preferred since they tend to collapse when wetted. Fibers such as a polyesters and polyamides are also resilient fibers so that they would aid in the expansion of the material upon dissolution of the hydrogen bonds. Such fibers may be produced by any method known in the art like spunbonding, meltblowing, solution spinning, etc. and may be blended by the conform process, the bonding carding process and the airlaying process, among others. The fibers may be from about 1 to about 10 denier in size and the material from about 1 osy (34 gsm) to about 4 osy (136 gsm). The material may be produced at a density of from about 0.15 g/cc to about 0.04 g/cc and compressed to a final density of up to about 0.3 g/cc. One method of compressing the material would be by hot pressing in a shimmed carver press at about 80 to 100° C. for about 1 minute. Another method would be through air bonding with a set of nip rolls at the exit to achieve the desired bulk. While other pressing procedures and other commercially available compressing procedures including continuous, on-line calendering, could also be utilized to produce the desired structures.

In this embodiment of the invention, the materials disclosed are also thin structures that include resilient fibers. These structures may be produced in an expanded low density state, and then fixed into a compressed state using a polymeric binding system which releases in the presence of moisture from the insult. When the binder releases, the resilient fibers should exhibit a degree of recovery and form a lower density web that would generate the void volume needed to manage the insult.

Moisture sensitive binders are available in powder, liquid, or fibrous form that may be activated using heat and/or small amounts of moisture. Binding systems may be polyvinyl alcohol adhesives, powders or fibers that dissolve in fluids. Some specific examples of polyvinyl alcohols have easily reversible crosslinks that allow changes in the adhesive property upon contact with the insult allowing the resilient structure to expand. Water sensitive hot melt adhesives could also be used that have time triggers based on controlled hydrophilicity or water triggerable polymers could be used such as base sensitive acrylics. Binders also include polyacrylic amides, polyacrylic acid and its copolymers, starch binders, cellulosic binders, and protein based binders.

In another embodiment of this invention, material structures are disclosed that include conjugate fibers which may be crimped. One side of the conjugate fiber may have a water triggerable first component such as polyethylene oxide while the other side of the fiber may have a resilient fiber second component such as polyethylene terephthalate (PET). With this type of fiber in web form, the structure should be able to both expand and contract depending on the level of moisture in the structure. The PET portion would keep the structure open for insults. Once the insult contacts the structure, the PEO fiber would activate. As the structure drains, the PEO should shrink and help the surge material return to a thin state. As time passes, the PEO should cause the surge to expand to be ready for the next insult. Over the life of the product, the structure should maintain a thin state more often than it is in an expanded state and therefore provide more comfort to the wearer. However, it can be in an expanded state often enough to manage the incoming insults. It is also possible to include superabsorbents in the material of this invention.

Many polymers are degradable in essentially plain water such as tap water which typically has a pH in the range of about 6.5 to about 8.5 and may serve as the water degradable portion of the conjugate fiber. Polymers can also be selected for the first component which are sensitive to or become degradable as a result of pH change, dissolved ion concentration change and/or temperature change in the aqueous environment.

Another mechanism which can be used to trigger water-degradability is ion sensitivity, where the term "ion" is given its conventional meaning of an atom or molecularly bonded group of atoms, which has gained or lost one or more electrons and consequently has a negative or positive electrical charge. Certain polymers contain acid-based (R—COO-) components which are held together by hydrogen bonding. In a dry state, these polymers remain solid. See for example, U.S. Pat. No. 4,419,403 to Varona which is incorporated herein by reference in its entirety.

Examples of polymers capable of degrading in aqueous mixtures or toilet water are poly (vinyl alcohol) graft copolymers supplied by the Nippon Synthetic Chemical Co., Ltd., Osaka, Japan, coded Ecomaty AX2000, AX10000 and AX-300G. Examples of such materials could also include NP2068, NP2074 or NP2120 aliphatic polyamides as supplied by the H. B. Fuller Company of Vadnais Heights, Minnesota. The Nippon polymers are cold water soluble but somewhat slower in their rate of solubility than the Fuller polymers. Yet another first component polymer could be a polyether block amide, coded Pebax MX1074, supplied by Atochem (USA) located in Philadelphia, Pa. The Pebax MX1074 polymer is composed of epsilon-caprolactam (Nylon 12) and tetramethylene glycol monomers. These monomers are polymerized to make a series of polyether block amide copolymers. The Pebax polymer is not water soluble but is water-swellable, and therefore could also be used in a higher water volume environment as well. The Fuller polymers can be matched to a second component (core) polymer with a softening or melting temperature at least about 10° C. higher, such as would be the case with polypropylene. The Nippon or Atochem polymers can be matched with a higher melting temperature range second component polymer such as polypropylene or poly (butylene terephthalate).

In any embodiment, the minimum amount of binder that would function is desirable and should be less than about 10 weight percent. If the binder is in fiber form it is preferable that the fibers be as fine as possible.

In its broadest definition the invention is a fibrous web which includes a binder and which is compressed to a density of up to about 0.3 g/cc. The web may preferably be formed by the bonded carded web process or air lay process. The binder may depend on hydrogen bonding using moisture or may be a non-aqueous solution, a powder, a fibrous binder or a conjugate fiber binder including a moisture triggerable component. Conjugate fibers may be crimped. When wetted the web of this invention should expand rapidly to greater than 80% of its uncompressed thickness and greater than 90% of its thickness when saturated if starting from the uncompressed state.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A surge material for personal care products comprising from about 20 to about 60 weight percent cellulosic fibers, from about 40 to about 80 weight percent resilient fibers compressed with a binder which releases in the presence of moisture to a density of up to about 0.3 g/cc, and having a high capillary force, wherein said material expands upon being wetted to greater than 80% of its uncompressed thickness, decreasing its density and generating void volume to provide retention capacity.

2. A personal care product comprising the material of claim 1.

3. The surge material of claim 1 wherein said resilient fibers are selected from the group consisting of polyolefin fibers, polyester fibers and polyamide fibers.

4. The surge material of claim 1 wherein said cellulosic fibers are selected from the group consisting of rayon fibers and cotton fibers having a denier between about 0.1 and 10.

5. A surge material for personal care products comprising fibers compressed with up to about 10 weight percent of a binder which releases in the presence of moisture selected from the group consisting of non-aqueous liquids, powders and fibers, to a density of up to about 0.3 g/cc, and having a high capillary force, wherein said material expands upon being wetted to greater than 80% of its uncompressed thickness, decreasing its density and generating void volume to provide retention capacity.

6. The surge material of claim 5 wherein said binder is selected from the group consisting of polyvinyl alcohols, polyacrylic amides, polyacrylic acid and its copolymers, starch binders, cellulosic binders, and protein based binders.

7. The surge material of claim 6 wherein said binder is a conjugate fiber comprising a first water triggerable component and a second component.

8. The surge material of claim 7 wherein said conjugate fibers are crimped.

9. The surge material of claim 8 wherein said crimped conjugate fibers comprise polyethylene terephthalate and polyethylene oxide.

10. The surge material of claim 6 which is produced by the air lay process.

11. The surge material of claim 6 which is produced by the bonded carded web process.

12. A personal care product selected from the group consisting of diapers, training pants, feminine hygiene products, absorbent underpants and adult incontinence products comprising the material of claim 6.

13. The product of claim 12 wherein said personal care product is an adult incontinence product.

14. The product of claim 12 wherein said personal care product is a feminine hygiene product.

15. The product of claim 12 wherein said personal care product is a diaper.

* * * * *

UNITED STATES PATENT AND TRADEMARK OFFICE
CERTIFICATE OF CORRECTION

PATENT NO. : 6,387,831 B2
DATED : May 14, 2002
INVENTOR(S) : Hannong Rhim et al.

It is certified that error appears in the above-identified patent and that said Letters Patent is hereby corrected as shown below:

Column 1,
Line 31, "conforms" should read -- coform --

Column 2,
Line 3, "conforms" should read -- coform --

Column 3,
Lines 24, 29, 31 and 32, "conforms" should read -- coform --

Column 5,
Line 38, "conforms" should read -- coform --

Signed and Sealed this

First Day of July, 2003

JAMES E. ROGAN
*Director of the United States Patent and Trademark Office*